United States Patent [19]

Pons Pons

[11] 4,425,302

[45] Jan. 10, 1984

[54] HOUSEHOLD ELECTRIC DEVICE, A SUBLIMER OF PERFUMED BARS AND/OR INSECTICIDES

[75] Inventor: Bartolomé Pons Pons, Madrid, Spain

[73] Assignee: Seimex, S.A., Barcelona, Spain

[21] Appl. No.: 347,504

[22] Filed: Feb. 10, 1982

[30] Foreign Application Priority Data

Dec. 17, 1981 [ES] Spain .............................. 262.127[U]

[51] Int. Cl.³ .......................... A61L 9/03; A01M 1/20; A01M 13/00
[52] U.S. Cl. ..................................... 422/125; 43/129; 219/275; 219/385; 219/459; 219/521; 219/544; 239/60; 239/136; 422/49; 422/187; 422/305; 422/306
[58] Field of Search ................. 422/49, 125, 123, 124, 422/187, 305, 306; 239/34, 53, 54, 56, 60, 136; 43/129; 219/275, 385, 459, 521, 544

[56] References Cited

U.S. PATENT DOCUMENTS

| | | | |
|---|---|---|---|
| 1,845,432 | 2/1932 | McRae et al. | 422/126 |
| 2,103,609 | 12/1937 | Bradburn | 239/54 |
| 2,611,068 | 9/1952 | Wellens | 422/125 X |
| 2,612,432 | 9/1952 | Boddy | 422/49 |
| 2,931,880 | 4/1960 | Yaffe | 422/125 X |
| 3,872,280 | 3/1975 | Van Dalen | 422/124 X |
| 3,902,877 | 9/1975 | Swaim | 422/123 X |

*Primary Examiner*—Barry S. Richman
*Attorney, Agent, or Firm*—Wenderoth, Lind & Ponack

[57] ABSTRACT

A household electric device, specifically a sublimer of perfumed bars and/or insecticides, includes a current receiving reservoir and a compartment in which a bar is housed, so that the bar gradually receives the heat necessary for the slow sublimation thereof. The reservoir has openings through which the vapors of the bar are discharged outwardly. The lateral sides of a central opening through which the vapors of the bar are discharged outwardly is provided with slots, blind at their ends, along which there is guided a manually-operated slide which incorporates a blade situated in the passage of the bar, constituting an element for removing the bar from the compartment in which it is housed. The free front of the casing is provided with holes in which there are disposed respective metal bushings covered with insulating sleeves. The metal bushings are connected to the plug of the assembly and to the heating resistance of the bar, and constitute receivers for another plug.

1 Claim, 2 Drawing Figures

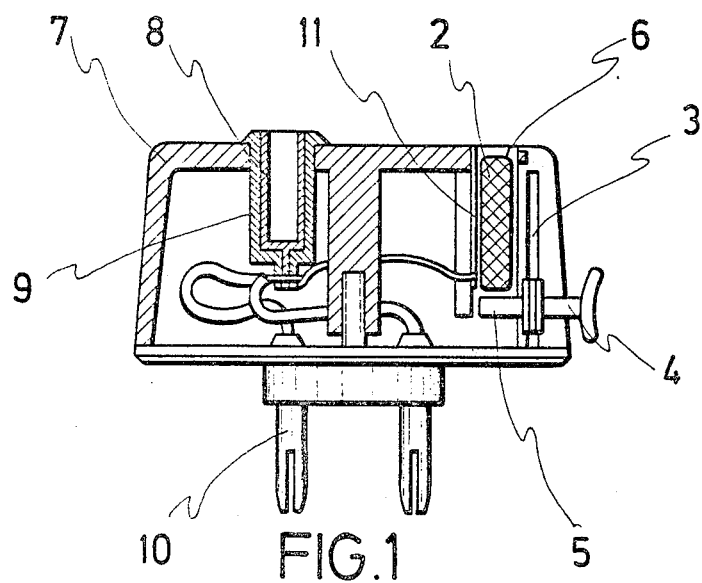
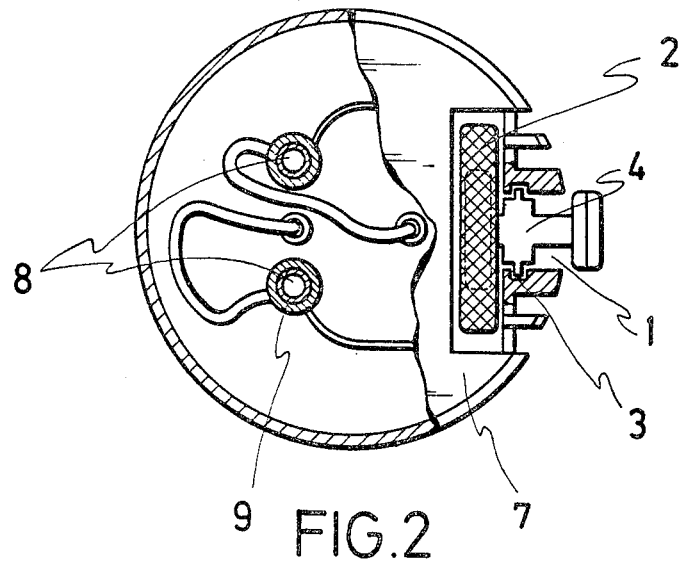

HOUSEHOLD ELECTRIC DEVICE, A SUBLIMER OF PERFUMED BARS AND/OR INSECTICIDES

BACKGROUND OF THE INVENTION

The present invention relates to an improved household electric device, a sublimer of perfumed bars and/or insecticides.

The act of subliming perfumed bars and/or insecticides by means of heat produced by an electrical resistance long has been known and carried out throughout the world, wherefore it can be considered as prior art inasmuch as there are patents covering this subject which have already lapsed.

However, modifications have been devised for the purpose of obtaining higher performance, of facilitating the manipulation thereof or of reducing the costs of the device and the assembly thereof, within the logical technical development which has day-by-day proportioned advantages bettering former designs.

With regard to the aforegoing, reference may be made to Spanish Utility Model No. 25,210, filed Dec. 1, 1950, claiming an electrical plug capable of containing a sublimable bar, which plug incorporates a current receiving reservoir for heating a resistance and is provided with a housing for the sublimable bar.

In other subsequent embodiments, such as in Spanish Utility Model No. 50,454, filed Oct. 11, 1955, the bar is housed in an independent part which, in turn, is coupled to the casing of the assembly. In Spanish Utility Model No. 51,144, filed Nov. 17, 1955, the casing is removed to replace used-up bars which are retained by means of gripping flanges.

The mentioned structures have been replaced by assemblies incorporating a tiltable removing system which protrudes outwardly of the apparatus, such as for example that claimed in Spanish Utility Model No. 241,342/6 which claimed priority from an Italian patent of Feb. 13, 1978.

All such devices, the main elements of which are in the public domain, comprise a casing in which there are housed the electric elements, the plug, holes for the circulation of the air, a housing for the sublimable bars and a removing system for replacing the used-up bars.

The main drawbacks presented by such devices and by those presently existing in the market involve, from an economical point of view, manufacture and assembly and, from a technical point of view, performance, efficiency and difficulty in removing the bar.

SUMMARY OF THE INVENTION

The design of the device of the present invention satisfactorily solves the mentioned drawbacks with respect to technical and commercial aspects while facilitating to a maximum the passage of air to favor the diffusion of the perfume and/or insecticide proportioned by the heating of the bar. Removal of the bar takes place rapidly and easily. However, the accidental removal thereof is not possible and there is no risk of the bar being deteriorated during insertion and removal thereof.

The device of the invention is of the type comprising a current receiving reservoir and a compartment in which the bar is housed, such that the bar gradually receives the heat necessary for the slow sublimation thereof. The reservoir has openings through which the vapors of the bar are discharged outwardly.

The most important characteristic resides in that the lateral sides of the central hole through which the vapors of the bar are discharged outwardly are provided with slots which are blind at their front ends and along which there is guided a hand operated slide which incorporates a blade situated in the passage of the bar, constituting an element for removing the bar from the compartment in which it is housed.

The free end of the casing is provided with holes in which there are arranged respective metal bushings covered with insulating sleeves. The metal bushings are connected to the plug of the assembly and to the heating resistance of the bar, and form receivers for another plug.

BRIEF DESCRIPTION OF THE DRAWINGS

In order to illustrate and describe further the above, reference now will be made to the following detailed description, with reference to the accompanying drawings which schematically represent an illustrative not limiting example of the present invention.

FIG. 1 is a cross-sectional view of the assembly of the invention, illustrating the main elements of which the device is comprised.

FIG. 2 is a partially sectioned plan view, emphasizing the configuration of a slide constituting a bar removing element and an arrangement of electric connecting elements.

DETAILED DESCRIPTION OF THE INVENTION

Referring to the drawings, shown therein are a central opening 1, a sublimable bar 2, blind slots 3, a slide 4, a removing blade 5, a compartment 6 in which the bar 2 is housed, a casing 7, metal bushings 8, insulating sleeve 9, a plug 10, and a heating resistance 11.

The casing 7 is provided with a series of openings which serve for the passage of vapors produced by the sublimable bar 2, of which openings central opening 1 has at its lateral sides slots 3 which are blind at their front ends. Along the slots 3 of the central opening 1 there is guided manually-operated slide 4 incorporating blade 5 which is situated in the passage of the bar 2 for the removal thereof from its compartment 6.

The free end of the casing 7 has holes occupied by the metal bushings 8 which are covered with insulating sleeves 9. The metal bushings 8 are connected to the plug 10 and to the resistance 11 for heating the sublimable bar 2.

Once the assembly is plugged into a current connector through the plug 10, the assembly can receive another plug in the metal bushings 8, so that the current connector is not exclusively occupied by the device, but it may be used for another electric apparatus.

The casing 7 is pivotable with respect to the base of the plug 10, since the metal bushings 8 are not rigidly fixed to plug 10 but are connected thereto by means of flexible electric conductors, wherefore the position of the bushings 8 can be adapted to the needs of the moment.

Insertion and removal of the sublimable bar 2 takes place very simply, since the insertion of bar 2 into the compartment 6 is effected directly and its penetration causes the displacement of the slide 4 to the bottom of the slots 3, while its removal takes place by manipulating the slide 4 which, through its blade 5, pushes the bar 2 outwardly.

I claim:

1. A household electrical device for sublimating a bar of a perfume or insecticide material, said device comprising:
- a casing defining a compartment dimensioned to receive therein a bar to be sublimated;
- an electric resistance positioned within said casing at a location adjacent said compartment;
- an electric plug attached to said casing and electrically connected to said resistance, such that when said plug is inserted into an electrical socket said resistance is heated, thereby sublimating the bar;
- said casing having openings including a central opening from said compartment for the discharge therefrom of vapors from the bar;
- said central opening having lateral sides having therein blind slots;
- a manually operable slide member slidably mounted in said slots;
- said slide member having a blade means extending into said compartment for, upon manual sliding of said slide member along said slots, slidably removing the bar from said compartment;
- said casing having an outer wall spaced from said plug, said outer wall having therein holes; and
- metal bushings covered with insulating sleeves positioned in said holes, said metal bushings being electrically connected to said plug and to said resistance, said metal bushings being dimensioned to receive another electric plug, such as that of another electrical apparatus.

* * * * *